United States Patent
Biadillah et al.

(10) Patent No.: US 11,872,134 B2
(45) Date of Patent: Jan. 16, 2024

(54) MEDICAL DEVICE USING BIOABSORBABLE MATERIAL

(71) Applicant: Xeltis, A.G., Zurich (CH)

(72) Inventors: Youssef Biadillah, Geneva (CH); Martijn Antonius Johannes Cox, Budel (NL)

(73) Assignee: Xeltis AG, Zurich (CH)

( * ) Notice: Subject to any disclaimer, the term of this patent is extended or adjusted under 35 U.S.C. 154(b) by 46 days.

(21) Appl. No.: 17/684,102

(22) Filed: Mar. 1, 2022

(65) Prior Publication Data
US 2022/0218481 A1    Jul. 14, 2022

Related U.S. Application Data

(63) Continuation of application No. 15/770,276, filed as application No. PCT/EP2016/075925 on Oct. 27, 2016, now Pat. No. 11,510,782.

(30) Foreign Application Priority Data

Oct. 27, 2015    (EP) .................................... 15191785

(51) Int. Cl.
*A61F 2/24*    (2006.01)
*A61L 27/50*    (2006.01)
*A61L 27/58*    (2006.01)

(52) U.S. Cl.
CPC ............ *A61F 2/2463* (2013.01); *A61F 2/246* (2013.01); *A61F 2/2412* (2013.01); *A61F 2/2454* (2013.01); *A61L 27/507* (2013.01); *A61L 27/58* (2013.01); *A61F 2210/0004* (2013.01); *A61F 2230/0013* (2013.01)

(58) Field of Classification Search
CPC ...... A61B 17/0057; A61B 2017/00575; A61B 2017/00597; A61B 2017/00601; A61B 2017/00606; A61B 2017/00628; A61F 2/2463; A61F 2/2412; A61F 2/2454; A61F 2/246; A61F 2210/0004; A61F 2230/0013; A61L 27/207; A61L 27/58
See application file for complete search history.

(56) References Cited

U.S. PATENT DOCUMENTS 9,877,852 B2 * 1/2018 Lavrijsen ................ A61L 27/56
2017/0072089 A1 * 3/2017 Nseir Manassa ....... C08L 67/04

* cited by examiner

*Primary Examiner* — Suba Ganesan
(74) *Attorney, Agent, or Firm* — LUMEN PATENT FIRM

(57) ABSTRACT

Bioabsorbable medical devices such as vascular closures, mitral chorea replacements, and mitral leaflet extensions are provided.

8 Claims, 9 Drawing Sheets

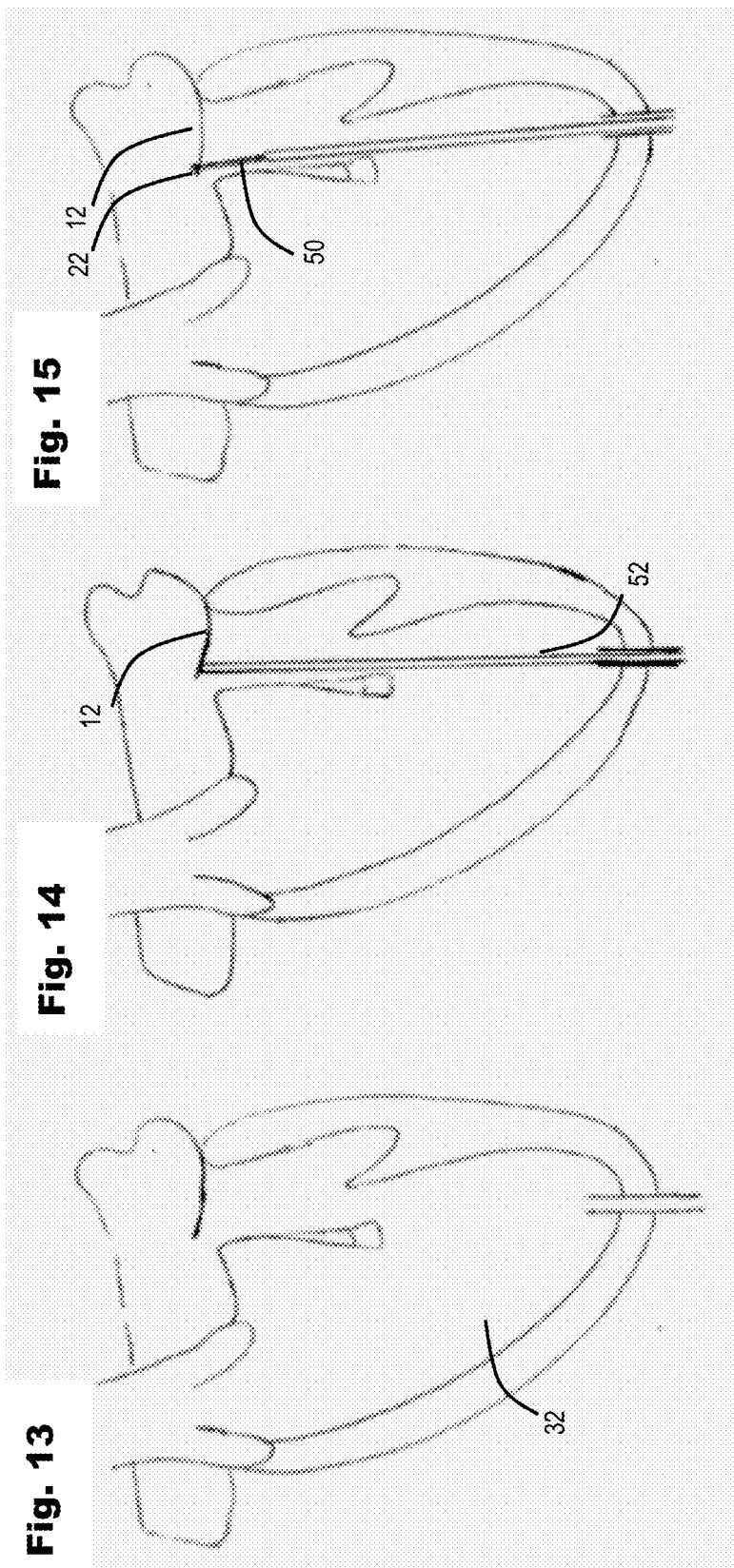

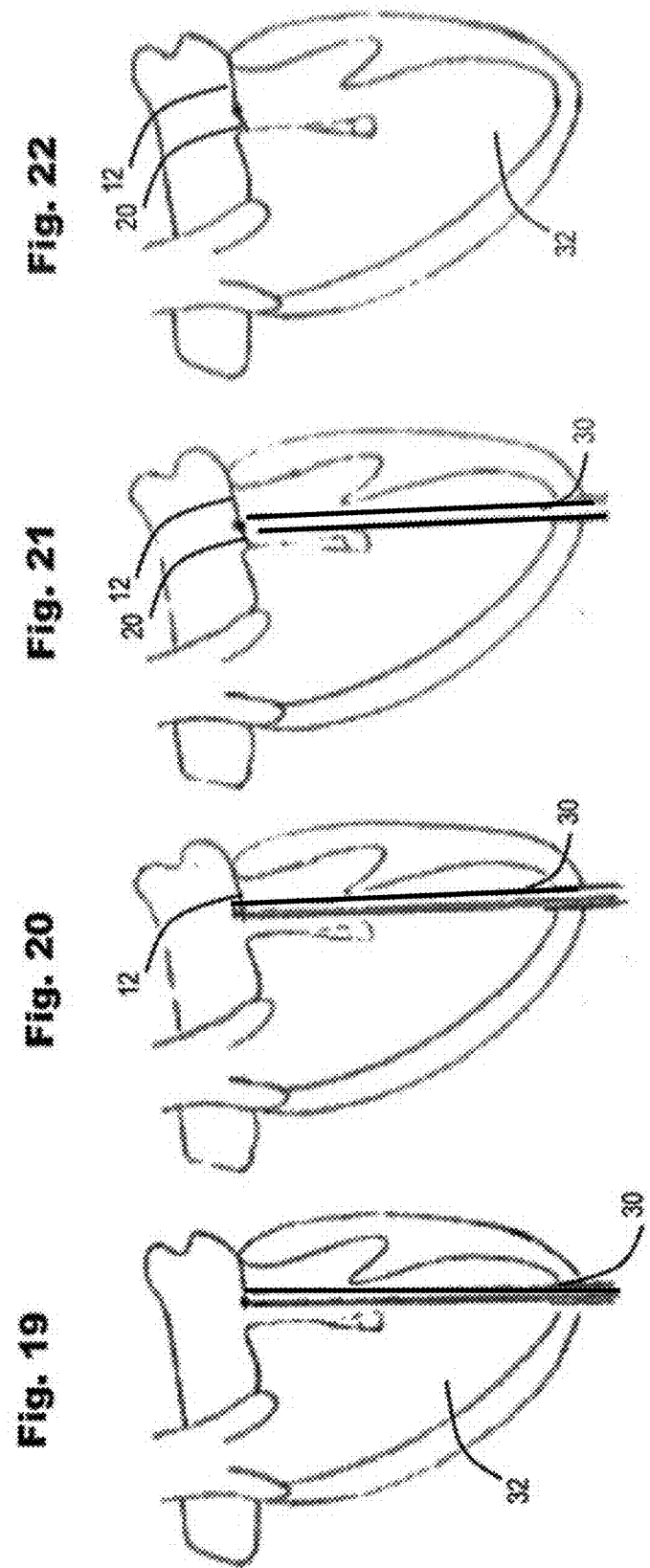

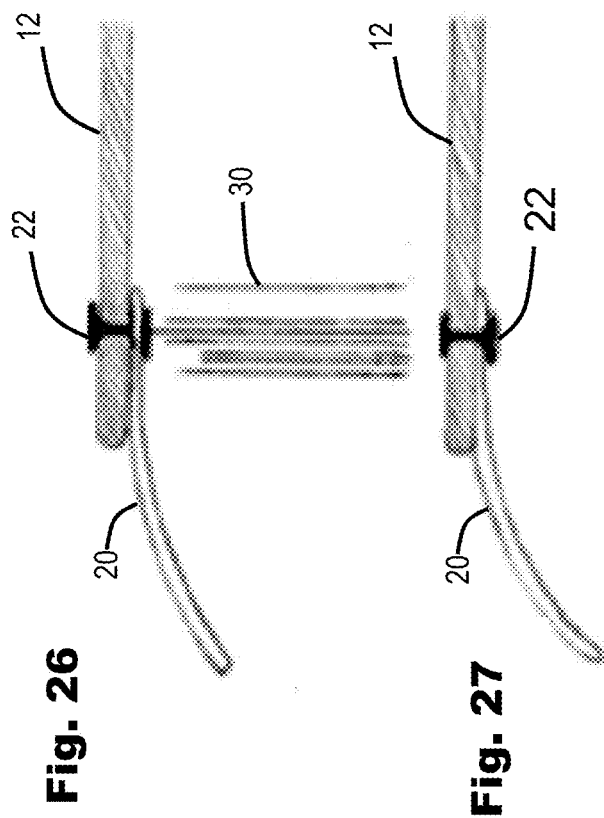
Fig. 26
Fig. 27
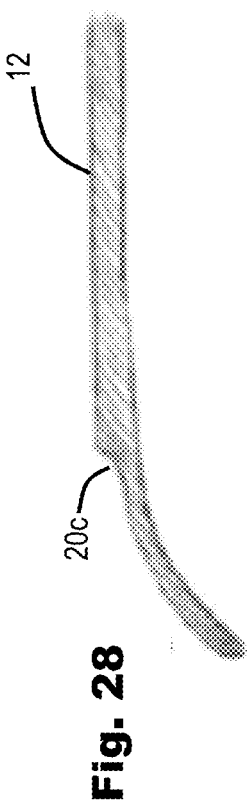
Fig. 28
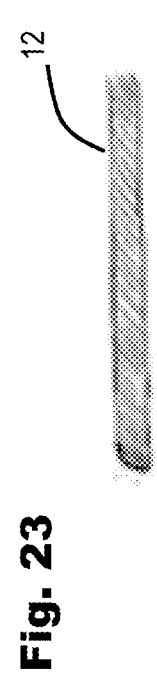
Fig. 23
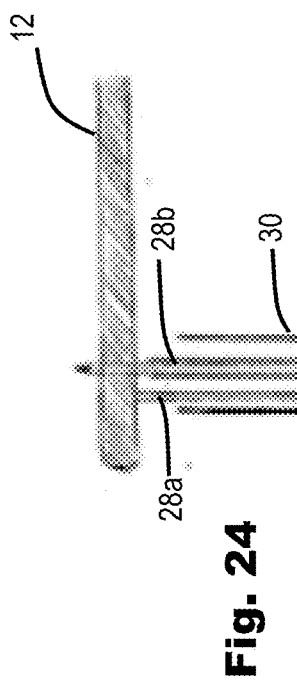
Fig. 24
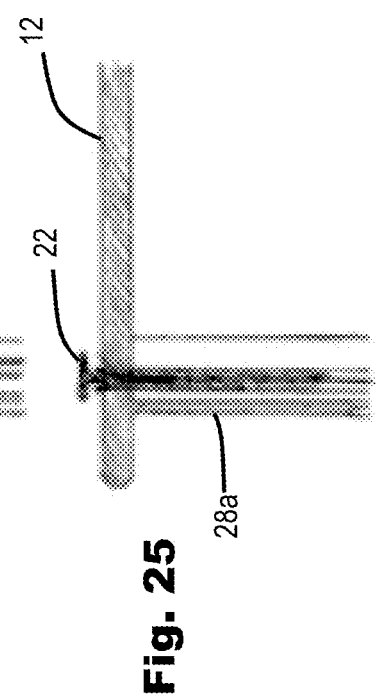
Fig. 25

MEDICAL DEVICE USING BIOABSORBABLE MATERIAL

CROSS-REFERENCE TO RELATED APPLICATIONS

This application is a continuation of U.S. patent application Ser. No. 15/770,276 filed Apr. 23, 2018, which is incorporated herein by reference. U.S. patent application Ser. No. 15/770,276 is a 371 of PCT application PCT/EP2016/075925 filed Oct. 27, 2016. PCT/EP2016/075925 claims benefit of EP application EP15191785.3 filed Oct. 27, 2015.

FIELD OF THE INVENTION

The invention relates to the field of medical devices. Some aspects of the invention relate to the use of bioabsorbable material. Example, but non-limiting, aspects of the invention relate to vascular closure devices, mitral chorea replacement, and mitral leaflet extension. These aspects are independent of each other, but any two or more may be used in combination if desired.

BACKGROUND OF THE INVENTION

In one aspect, the mitral valve is one of heart's valves controlling blood flow into the left ventricle. Mitral valve regurgitation is a functional deficiency that occurs when the leaflets fail to close appropriately to block reverse flow of blood through the valve.

Ischemia and a dilated left ventricle resulting in separation of the mitral leaflets and consequent lack of leaflet coaptation, is one cause of functional mitral regurgitation. Mitral valve leaflet prolapse is another, and is said to be the most common cause of severe, non-ischemic mitral regurgitation. This is often due to rupture of the mitral chordae that support the mitral valve.

Mitral valve repair is generally considered preferable to replacement. Current ACC/AHA guidelines promote repair of mitral valve in patients before symptoms of heart failure develop. Symptomatic patients, those with evidence of diminished left ventricular function, or those with left ventricular dilatation need urgent attention.

Various treatment methods are available such as mitral valve repair, annuloplasty rings, and mitral valve replacement. However, disadvantages of current techniques include: generally invasive procedures; significant amounts of foreign material being left in the body; and many methods limiting options for future treatments.

A related aspect of this disclosure may relate to vascular access for vascular interventions (including, for example, vascular access to the heart). The description of the Seldinger technique in 1953 created a novel problem; physicians were creating holes in arteries that now needed to be closed. The first, and still gold standard, method for addressing this problem was the use of manual compression. As the holes got bigger and constraints on physicians' time became greater, novel solutions to this problem, called vascular closure devices VCDs, began to emerge.

Over 10,000,000 vascular interventions are performed worldwide each year but still only about a third of them use VCDs while in the rest manual compression is still used. The limited use of presently available VCDs is due to a lack of clear demonstrated benefit for VCDs in reducing bleeding and vascular complications when compared to manual compression, the continued requirement for post-procedure bed rest, complexity in device deployment often resulting in a long learning curve (a particular problem for low-volume operators), and cost.

A further disadvantage is that current designs of VCD severely restrict the possibility of using the same access site for re-intervention. Most VCDs are made of either 1) non-biodegradable material, or 2) bioabsorbable material with no or only low structural integrity (e.g. gels). Use of a non-biodegradable material permanently obstructs the access site, thereby eliminating any possibility of being able to reuse the same access site in the future. Use of a bioabsorbable material of low structural integrity may not obstruct the access site permanently, but the lack of structural support makes it hazardous to re-use the same or even an adjacent access site for re-intervention until the tissue has properly healed, which may take weeks or even months.

SUMMARY OF THE INVENTION

It would be desirable to address and/or mitigate at least one of the aforementioned issues.

The following presents a summary to provide an understanding of some aspects of the invention. This summary is not an extensive overview of the invention. It is intended to neither identify key or critical elements of the disclosure nor delineate the scope of the invention. Its sole purpose is to present some concepts of the invention in a simplified form as a prelude to the more detailed description that is presented later.

One aspect of the present disclosure may provide a prosthetic mitral leaflet extension comprising bioabsorbable material.

Another aspect of the present disclosure may provide use of a bioabsorbable material as a mitral leaflet extension.

In such aspects, the mitral leaflet extension (or plural extensions, if plural extensions are used in combination) may optionally be configured to, and/or may serve to, close a gap between the two native leaflets and/or provide good coaptation. The native mitral valve leaflet(s) may continue to function, with a larger surface provided by the extension(s). The extension may be a prosthetic extension of the existing mitral leaflet.

Advantages of such aspects include one or more of: (i) minimal disruption to the heart anatomy; (ii) reduction in the amount of foreign material resulting from the prosthetic device, because the bioabsorbable material will disappear as it is progressively absorbed by the body and new tissue grows in its place; (iii) ability to retain options for future treatments of the heart and/or the mitral valve; and (iv) ability to implant the prosthetic extension using a non-invasive technique.

The prosthetic extension may be configured to be attached directly to the native valve leaflet without extra-leaflet anchoring, e.g. without the need for anchoring beyond the native leaflet itself. The use of bioabsorbable material may make this feasible. The bioabsorbable material is absorbed as the natural tissue grows, thereby creating a strong and durable attachment, and avoiding leakage of blood between the native leaflet and the prosthetic extension.

Additionally or alternatively, the mitral leaflet extension may be attached to the ventricular side of the native leaflet. Mounting the extension on the ventricular side may use the blood pressure within the ventricle during systole to press the extension against the native leaflet. This may (i) reduce risk of leakage between the native leaflet and the extension, and/or (ii) encourage growth of leaflet tissue from the native leaflet into the extension. Alternatively, if desired, the extension may be mounted to the atrial side of the native leaflet.

Additionally or alternatively to any of the above, the bioabsorbable material may provide structural integrity for the leaflet extension. For example, the bioabsorbable material may provide a load-bearing structure for the leaflet extension.

The bioabsorbable material may have a tensile strength at least about 1 MPa, optionally at least about 5 MPa, optionally at least about 10 MPa, optionally at least about 20 MPa, optionally at least about 50 MPa.

The bioabsorbable material may have a suture retention capability of at least about 1 Newton, optionally at least about 2 Newton, optionally at least about 5 Newton, optionally at least about 10 Newton.

The bioabsorbable material may have a degradation rate after implantation in the body such that the bioabsorbable material retains its structural integrity for at least about 1 month, optionally least about 2 months, optionally at least about 3 months, optionally at least about 4 months, optionally at least about 5 months, optionally at least about 6 months. Structural integrity may be assessed by, for example, the bioabsorbable material retaining least 50% of its mass for the specified time, and/or retaining at least about 50% of its tensile strength for the specified time.

The material may be, but is not limited to, a bioabsorbable electrospun polymer or a matrix with one or more supramolecular compounds. The matrix may be comprised of a fibrous network and at least 90% porosity, or at least 80% porosity, or at least 70% porosity, or at least 60% porosity.

In some embodiments, the leaflet extension is made of a bioabsorbable material geometrically shaped to close the gap between the two mitral leaflet and anchors attached to secure the leaflet extension onto the native leaflet.

Optionally, a single leaflet extension may be implanted. Alternatively, one may implant two leaflet extensions with each one attached to each mitral leaflet. For example, in some cases, plural leaflet extensions may facilitate optimal valve dynamics.

Another aspect of the present disclosure may provide a prosthetic chordae comprising bioabsorbable material.

Another aspect of the present disclosure may provide use of a bioabsorbable material as a chordae replacement.

In such aspects, the bioabsorbable material may provide structural integrity for the prosthetic or replacement mitral chordae. For example, the bioabsorbable material may provide a load-bearing structure for the chordae.

The bioabsorbable material may have a tensile strength at least about 1 MPa, optionally at least about 5 MPa, optionally at least about 10 MPa, optionally at least about 20 MPa, optionally at least about 50 MPa.

The bioabsorbable material may have a suture retention capability of at least about 1 Newton, optionally at least about 2 Newton, optionally at least about 5 Newton, optionally at least about 10 Newton.

The bioabsorbable material may have a degradation rate after implantation in the body such that the bioabsorbable material retains its structural integrity for at least about 1 month, optionally least about 2 months, optionally at least about 3 months, optionally at least about 4 months, optionally at least about 5 months, optionally at least about 6 months. Structural integrity may be assessed by, for example, the bioabsorbable material retaining least 50% of its mass for the specified time, and/or retaining at least about 50% of its tensile strength for the specified time.

The material may be, but is not limited to, a bioabsorbable electrospun polymer or a matrix with one or more supramolecular compounds. The matrix may be comprised of a fibrous network and at least 90% porosity, or at least 80% porosity, or at least 70% porosity, or at least 60% porosity.

The chordae replacement may be made of various including but not limited to a thread, multiple interwoven threads, a woven textile, a ribbon, a helix, a coil, or a combination thereof.

Another aspect of the disclosure may provide a VCD comprising bioabsorbable material.

The bioabsorbable material may provide structural integrity for the VCD. For example, the bioabsorbable material may provide a load-bearing structure of the VCD.

The bioabsorbable material may have a tensile strength at least about 0.1 MPa, optionally at least about 0.5 MPa, optionally at least about 1 MPa, optionally at least about 5 MPa, optionally at least about 10 MPa, optionally at least about 20 MPa, optionally at least about 50 MPa.

The bioabsorbable material may have a suture retention capability of at least about 0.5 Newton, optionally at least about 1 Newton, optionally at least about 2 Newton, optionally at least about 5 Newton, optionally at least about 10 Newton.

The bioabsorbable material may have a degradation rate after implantation in the body such that the bioabsorbable material retains its structural integrity for at least about 1 week, optionally at least about 2 weeks, optionally at least about 1 month, optionally least about 2 months. Structural integrity may be assessed by, for example, the bioabsorbable material retaining least 50% of its mass for the specified time, and/or retaining at least about 50% of its tensile strength for the specified time.

The VCD may be made at least partly of the material, or at least a majority of the VCD may be of the material, or substantially all of the VCD may be of the material.

The material may be, but is not limited to, a bioabsorbable electrospun polymer or a matrix with one or more supramolecular compounds. The matrix may be comprised of a fibrous network and at least 90% porosity, or at least 80% porosity, or at least 70% porosity, or at least 60% porosity.

The VCD, once deployed may optionally comprise a shape selected from, but not limited to, a dumbbell, a cork, a double parachute, an hourglass shape, or zig-zag shaped ribbon, or a plug, a rivet, or any combination of two or more of these shapes.

The VCD may also be used in conjunction with sutures, which could in turn be biodegradable and or thin biodegradable rods, for added safety and enhanced control.

BRIEF DESCRIPTION OF THE DRAWINGS

FIGS. 13 to 18 are schematic drawings illustrating an example implantation procedure of chordae replacement. The illustrations detail the case of the implantation of a loop (dual threads).

FIGS. 19 to 22 are schematic drawings illustrating an example implantation procedure using a leaflet extension prosthesis. The illustrations detail the case of the implantation of one leaflet extension.

FIGS. 23 to 26 are schematic drawings showing in more detail some of the steps of FIGS. 19 to 22 viewed at the native leaflet.

FIG. 27 is a schematic drawing illustrating a portion of a mitral leaflet with the prosthetic extension immediately after implantation.

FIG. 28 is a schematic drawing similar to FIG. 27 but showing the state of the native tissue after a certain time allowing integration of the extension with respect to the leaflet tissue.

DETAILED DESCRIPTION

Figure 29:
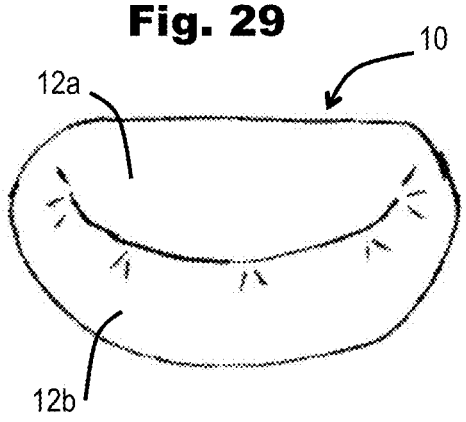
FIG. 29 is a schematic plan view of an example healthy mitral valve.
Figure 30:
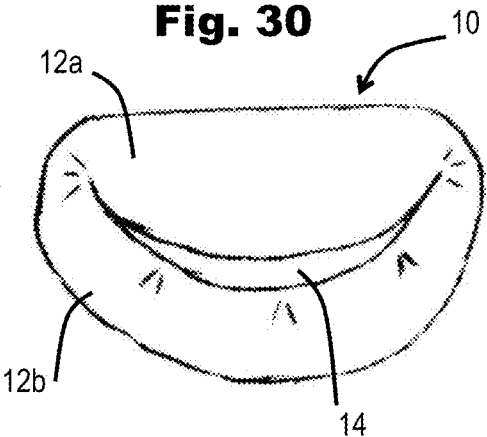
FIG. 30 is a schematic plan view of an example dysfunctional mitral valve.

Mitral Leaflet Extension Referring to FIG. 29, a healthy mitral valve 10 is illustrated, formed by two native leaflets 12 called the anterior leaflet 12a and posterior leaflet 12b. In a healthy valve 10, during systole, the leaflets 12 coapt to close the valve aperture against back-flow of blood. FIG. 30 illustrates one example of a dysfunctional mitral valve in which the leaflets 12 fail to coapt, for example, as result of ischemia or left ventricle dilation. A gap 14 remains between the leaflet surfaces, leading to regurgitation of blood through the valve aperture under systole.

Figure 31:
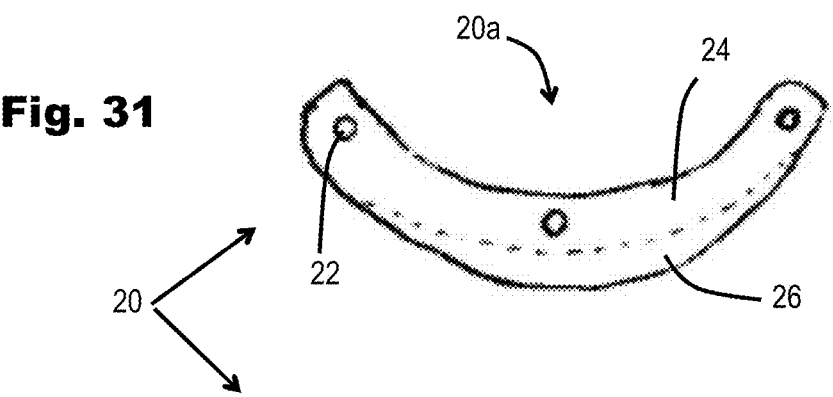
FIGS. 31 and 32 are schematic plan views of example mitral leaflet extensions for anterior and posterior native mitral leaflets.
Figure 32:
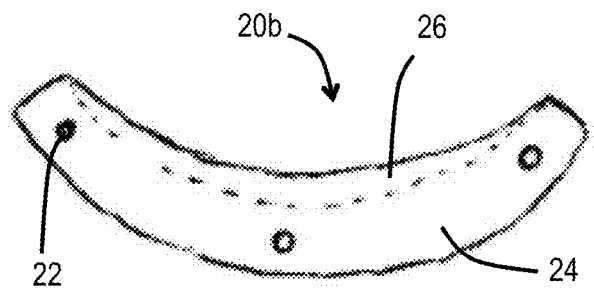
Figure 33:
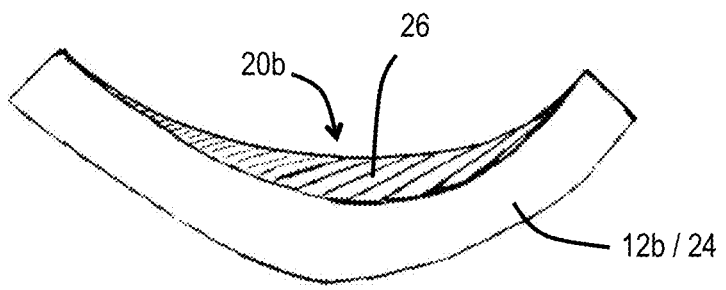
FIG. 33 is a schematic drawing illustrating a mitral leaflet to which the extension is attached.

Referring additionally to FIGS. 31-33, some embodiments of the present disclosure may provide a prosthetic mitral leaf extension 20 comprising bioabsorbable material.

Additionally or alternatively, some embodiments of the present disclosure may provide use of a bioabsorbable material as a mitral leaflet extension 20.

In such embodiments, the mitral leaflet extension 20 (or plural extensions, if plural extensions are used in combination) may optionally be configured to, and/or may serve to, close a gap 14 between the two native leaflets 12 and/or provide good coaptation. The native mitral valve leaflet(s) 12 may continue to function, with a larger surface provided by the extension(s) 20. The extension 20 may be a prosthetic extension of the existing mitral leaflet 12.

The prosthetic extension 20 may be configured to be attached directly to the native valve leaflet 12 without extra-leaflet anchoring, e.g. without the need for anchoring beyond the native leaflet itself. The use of bioabsorbable material may make this feasible. The bioabsorbable material is absorbed as the natural tissue grows, thereby creating a strong and durable attachment, and avoiding leakage of blood between the native leaflet and the prosthetic extension. The prosthetic extension 20 may become absorbed or integrated into the native leaflet as new tissue grows from the native leaflet 12. FIG. 28 illustrates an example of how the prosthetic extension is integrated into native leaflet tissue 20c over time, compared with an initially implanted condition in FIG. 27). In contrast, a leaflet extension made of non-bioabsorbable material (e.g. PTFE or ePTFE) might not be as feasible without using extra-leaflet anchoring, because the leaflet attachment would be unlikely to endure the unceasing movement of the leaflet, leading to risk of catastrophic detachment with time, worsening regurgitation with time, or even further damaging the delicate native leaflet tissue.

Additionally or alternatively, the mitral leaflet extension 20 may be attached to the ventricular side of the native leaflet 12. Mounting the extension on the ventricular side may use the blood pressure within the ventricle during systole to press the extension against the native leaflet. This may (i) reduce risk of leakage between the native leaflet and the extension, and/or (ii) encourage growth of leaflet tissue from the native leaflet into the extension. Alternatively, if desired, the extension may be mounted to the atrial side of the native leaflet.

In some embodiments, the leaflet extension 20 is made of a bioabsorbable material geometrically shaped to close the gap 14 between the two mitral leaflets 12, and one or more optional anchors 22 attached to secure the leaflet extension 20 onto the native leaflet 12.

FIGS. 31 and 32 illustrate example mitral leaflet extension prostheses 20a and 20b respectively for the anterior leaflet 12a and posterior leaflet 12. Each prosthesis 16 may include an interface or attachment zone 24 intended to overlap with and/or attach to the native leaflet tissue. Additionally or alternatively, each prosthesis may include an extension zone 26 intended to provide the larger area surface projecting beyond the periphery of the native leaflet. The zones 24 and 26 may be integral with each other, such that the zones 24 and 26 are collectively a continuous body of material.

The prosthesis 20 may have a generally arcuate shape, optionally a crescent shape, although other shapes may be used as desired. Additionally or alternatively, at least one, optionally both, of the zones 24 and 26 may have a generally arcuate shape, optionally a crescent shape, although other shapes may be used as desired. Referring to FIG. 31, for the extension prosthesis 20a for an anterior leaflet 12a, the extension zone 26 may optionally be on a convex edge of the attachment zone 24 and/or the attachment zone 24 may be on a concave edge of the extension zone 26. Referring to FIG. 32, for the extension prosthesis 20b for a posterior leaflet 12b, the extension zone 26 may optionally be on a cocave edge of the attachment zone 24 and/or the attachment zone 24 may be on a convex edge of the extension zone 26.

The zones 24 and 26 may be distinguished from each other (e.g. by having one or more different properties), or the zones 24 and 26 may have the same properties. If provided, one or more optional anchors 22 may be pre-attached at the attachment zone 24. The anchors 22 are depicted schematically; more detail is explained later below.

By way of example, FIG. 33 illustrates a portion of the posterior leaflet 12b to which a prosthesis 20b has been attached. The attachment zone 24 overlaps a peripheral region of the native leaflet 12b, and the extension zone 26 provides additional surface beyond the periphery of the native leaflet tissue, for coapting with the opposite anterior leaflet (which may optionally also carry a prosthetic extension).

The bioabsorbable material may provide structural integrity for the leaflet extension 20. For example, the bioabsorbable material may provide a load-bearing structure for the leaflet extension.

The bioabsorbable material may have a tensile strength at least about 1 MPa, optionally at least about 5 MPa, optionally at least about 10 MPa, optionally at least about 20 MPa, optionally at least about 50 MPa.

The bioabsorbable material may have a suture retention capability of at least about 1 Newton, optionally at least about 2 Newton, optionally at least about 5 Newton, optionally at least about 10 Newton.

The bioabsorbable material may have a degradation rate after implantation in the body such that the bioabsorbable material retains its structural integrity for at least about 1 month, optionally least about 2 months, optionally at least about 3 months, optionally at least about 4 months, optionally at least about 5 months, optionally at least about 6 months. Structural integrity may be assessed by, for example, the bioabsorbable material retaining least 50% of its mass for the specified time, and/or retaining at least about 50% of its tensile strength for the specified time.

The material may be, but is not limited to, a bioabsorbable electrospun polymer or a matrix with one or more supramolecular compounds. The matrix may be comprised of a fibrous network and at least 90% porosity, or at least 80% porosity, or at least 70% porosity, or at least 60% porosity.

The bioabsorbable material may be, but is not limited to a bioabsorbable electrospin polymer with a fiber diameter of 1 micrometer to 50 micrometers or optionally 3 micrometers to 20 micrometers or optionally 4 micrometers to 15 micrometers.

The bioabsorbable material may be, but is not limited to, a bioabsorbable electrospun polymer with a poresize in between 1 to 300 micrometers or optionally 5 to 100 micrometers, and allowing cell infiltration and cell ingrowth throughout the thickness of the material.

The bioabsorbable material may be, but is not limited to, a material with coefficient of friction below 0.8, optionally below 0.5, optionally below 0.3.

The bioabsorbable material may be, but is not limited to, a material which combined properties allow it to be compressed and delivered through a catheter via minimal invasive surgery, in a way that is not possible today. This could mean either that more material can be used with same catheter size compared to other approaches, or that a smaller catheter size can be used compared to other approaches. The combined properties may include, but are not limited to, porosity, stiffness, coefficient of friction, thickness and/or suture retention strength.

The bioabsorbable material may be constructed with a gradient in properties, but is not limited to that. The gradient could run through the thickness of the material as well as over the surface of the material. The property gradients may include stiffness, thickness, fiber diameter, fiber alignment, absorption and/or porosity, or a combination of these factors.

The bioabsorbable material may be constructed with local variations in properties, but is not limited to that. An example of a local variation in properties may be a local variation in thickness, fiber diameter, fiber alignment, fiber porosity, stiffness or suture retention strength, or a combination of these properties, for example with the goal of creating a local reinforcement around a suture hole or around the attachment point to the surrounding native tissue. In another example, the local variation in properties may be used to accommodate local variations in mechanical loads during the in vivo performance of the device.

Referring to FIGS. 19 to 28, in some embodiments, an example implantation technique may generally pertain to, but is not limited to, inserting a delivery system 30 through the apex of the heart into the left ventricle 32 (FIG. 19), grabbing one mitral leaflet 12 using a grabber 28*a* (FIGS. 20 and 24), piercing through the leaflet 12 using a piercing element 28*b* (FIG. 24) and inserting and deploying the distal end (atrial side) of an anchor 22 (FIG. 25), deploying the proximal end (ventricular side) of the anchor 22 and releasing the leaflet extension section or prosthesis 20 attached to the anchor 22 (FIGS. 21 and 26). The implantation may pertain to deploying either one or multiple anchors 22 to fully deploy and release the entire leaflet prosthetic extension 20. Sequential attachment using multiple anchors 22 is, for example, illustrated schematically in FIGS. 34-36. Once the extension 20 has been attached and fully released, the delivery system 30 is removed, and the heart apex closed to seal the ventricle 32 (FIG. 22).

FIG. 27 illustrates an example of the implanted prosthetic extension 20 immediately after implantation, and FIG. 28 illustrates how, over time, the prosthetic extension 20 may become absorbed or integrated into the native leaflet as new tissue 20*c* grows from the native leaflet 12.

Optionally, a single leaflet extension 20 may be implanted. Alternatively, one may implant two leaflet extensions 20 (20*a* and 20*b*) with each one attached to a respective mitral leaflet 12*a* and 12*b*. For example, in some cases, plural leaflet extensions 20 may facilitate optimal valve dynamics. The implantation may also be performed using a different access other than the transapical access if a different access site is preferred.

Grabbing of the leaflet may be performed by various grabbers 28*a* or means, including but not limited to, deployment of two fingers to clamp onto the leaflet or bringing a suction device close to the leaflet to grab it.

The anchor(s) 22 once deployed may be or comprise varying shapes, including but not limited to, dumbbells, double parachutes, hourglass shapes, rivets, or any combination of two or more of these shapes. FIGS. 23 to 28 are schematic drawings illustrating deployment of an example anchor shaped as a dumbbell.

In some embodiments, the anchor(s) 22 may be made of or comprise a shape memory alloy such as nitinol and/or may be made of or comprise a bioabsorbable material, for example, polyethylene glycol.

In some embodiments, the anchor(s) 22 may also be made of the same material as the leaflet extension 20 itself and secured using sutures or another means.

In some embodiments, the leaflet extension 20 may not have any anchors and could be simply attached to the native leaflet 12 by means of sutures.

Figure 34:
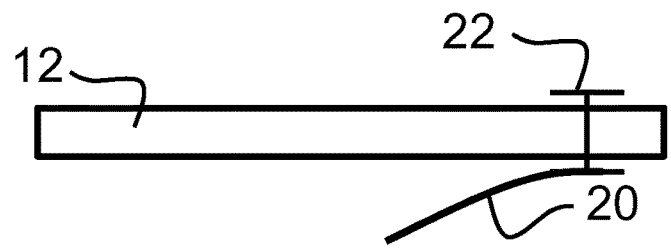
FIGS. 34 to 36 are schematic drawings illustrating implantation of a prosthesis having pre-attached anchors.
Figure 35:
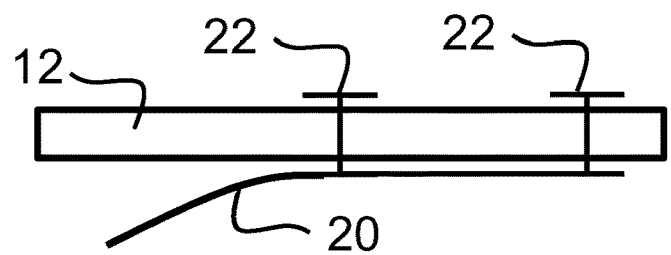
Figure 36:
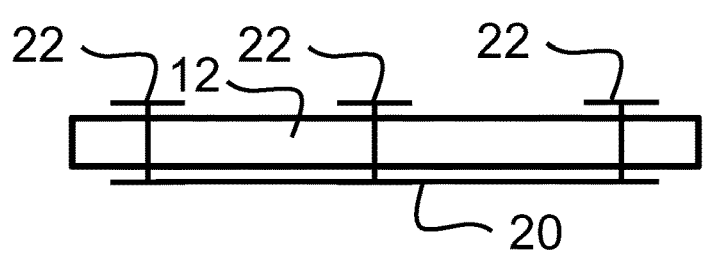
Figure 37:
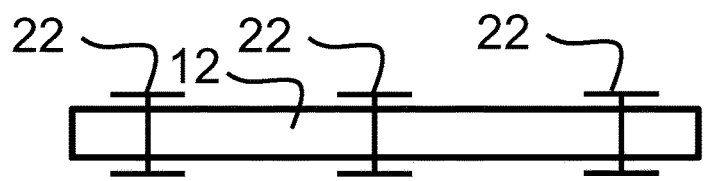
FIGS. 37 to 40 are schematic drawings illustrating implantation of a prosthesis without pre-attached anchors.
Figure 38:
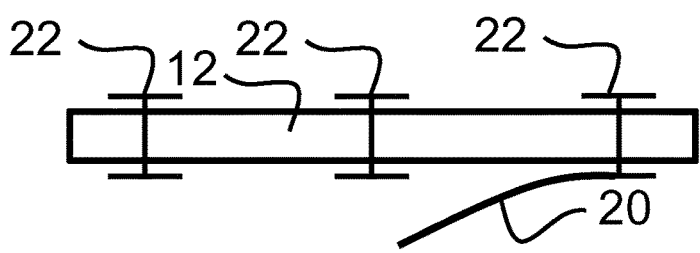
Figure 39:
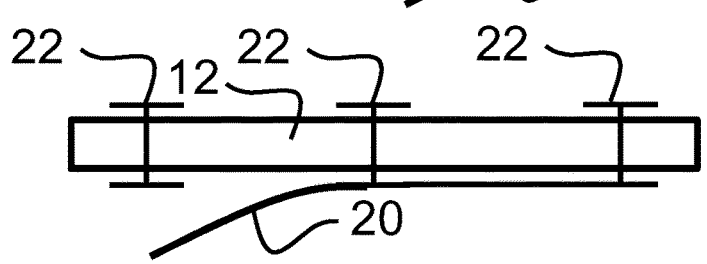
Figure 40:
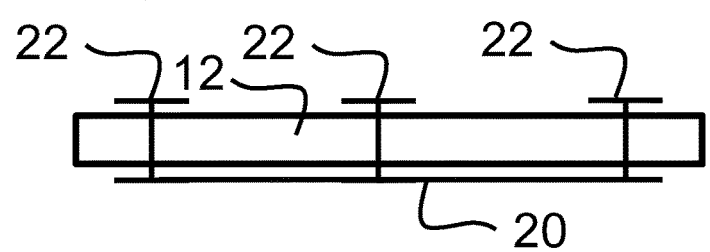

In the implantation technique illustrated in FIGS. 19-28 and also represented in FIGS. 34 to 36, the anchor(s) 22 may be pre-attached to the prosthetic leaflet extension 20 before implantation, for example, either during manufacture of the prosthesis 20, or in a preparation procedure just prior to the implantation procedure. Alternatively, as illustrated in FIGS. 37-40, the anchor(s) 22 may be separate from the prosthesis 20, and attached initially to the native leaflet tissue 12 in an initial step of the implantation procedure (FIG. 37). Thereafter, the extension prosthesis 20 may be brought to the native tissue 12, and attached to the anchors 22 that have now been mounted to the native tissue 12. FIGS. 38 to 40 illustrate sequential attaching of the prosthetic extension 20 to three anchors 22. The prosthesis 20 may be coupled to the anchors 22 by any suitable technique, for example, by snapping or clipping the prosthesis to the anchors 22, or by magnetic attachment.

Figure 41:
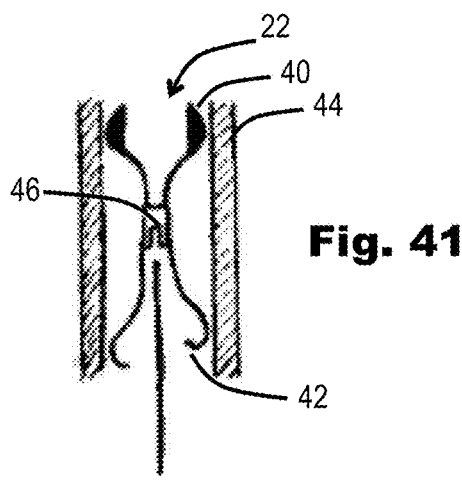
FIGS. 41 and 42 are schematic side views of an example anchor in a collapsed and deployed condition, respectively.
Figure 42:
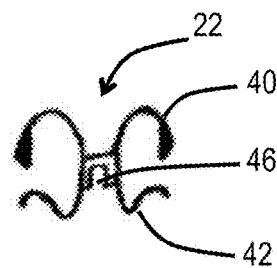

FIGS. 41 and 42 illustrate an alternative example of anchor 22 associated with the procedure of FIGS. 37-40, but the same anchor design could also be used for pre-attached anchors 22. Referring to FIGS. 41 and 42, the anchor 22 includes sharp distal fingers 40 extending from one end, and proximal fingers 42 extending from the opposite end. The anchor is made of a material (e.g. shape memory alloy or plastics) that is able to deform to a collapsed condition when sheathed in a delivery sheath 44 (FIG. 41), and return to its expanded condition when unsheathed (FIG. 42). The anchor 22 also includes a releasable coupling element 46 enabling the anchor 22 to be releasably coupled to a delivery system.

Figure 43:
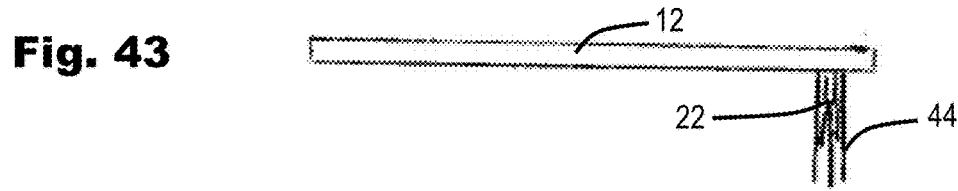
FIGS. 43 to 47 are schematic drawings illustrating a procedure for affixing the anchor of FIGS. 41 and 42 to native leaflet tissue.
Figure 44:
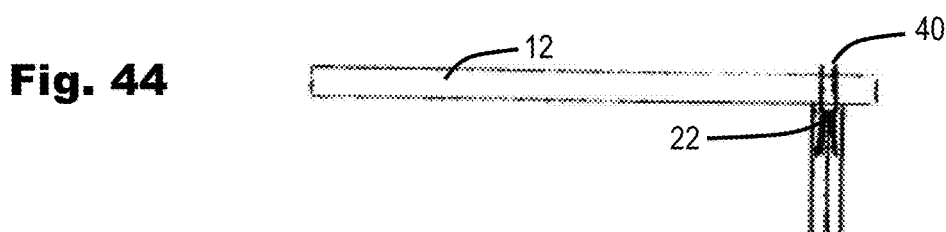
Figure 45:
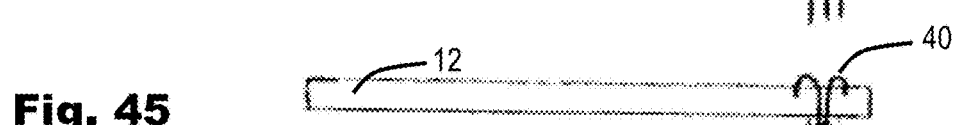
Figure 46:
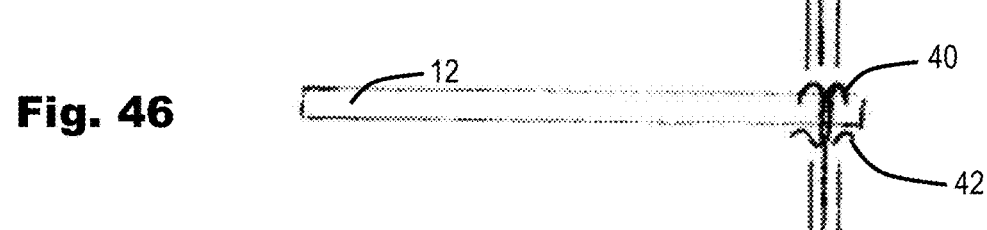
Figure 47:
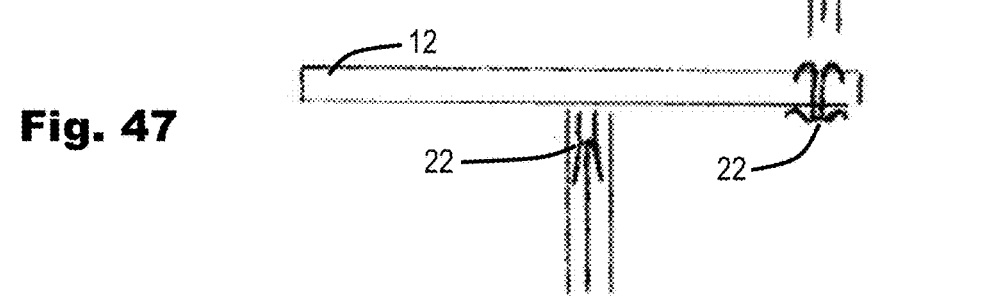

FIGS. 43 to 47 illustrate a technique for mounting the anchors 22 to the native leaflet tissue 12. A delivery sheath 44 containing the anchor 22 in its collapsed condition is brought into contact with the native leaflet 12 (FIG. 43). This can be done mechanically and simply visually or can be done with other means such as applying suction. The sharp distal fingers 40 may then be advanced to pierce through the native leaflet tissue 12 (FIG. 44). The sharp distal fingers 40 may then be fully unsheathed to allow them to deploy on the distal side of the leaflet 12 (FIG. 45). The proximal fingers 44 may then be fully unsheathed to allow them to deploy on the proximal side of the leaflet 12 (FIG. 46). The anchor 22 may then be released from the delivery system by means of the coupling element 46 (for example, either clipped or unscrewed from a cable or shaft running through the delivery system). The process may then be repeated for a next anchor 22 (FIG. 47).

Mitral Chordae Replacement

Alternatively or additionally, some other embodiments of the present disclosure may provide a prosthetic chordae comprising bioabsorbable material.

Additionally or alternatively, some embodiments of the present disclosure may provide use of a bioabsorbable material as a chordae replacement.

Referring to FIGS. 13 to 18, in such embodiments, the bioabsorbable material may provide structural integrity for the prosthetic or replacement mitral chordae 50. For example, the bioabsorbable material may provide a load-bearing structure for the chordae 50.

The bioabsorbable material may have a tensile strength at least about 1 MPa, optionally at least about 5 MPa, optionally at least about 10 MPa, optionally at least about 20 MPa, optionally at least about 50 MPa.

The bioabsorbable material may have a suture retention capability of at least about 1 Newton, optionally at least about 2 Newton, optionally at least about 5 Newton, optionally at least about 10 Newton.

The bioabsorbable material may have a degradation rate after implantation in the body such that the bioabsorbable material retains its structural integrity for at least about 1 month, optionally least about 2 months, optionally at least about 3 months, optionally at least about 4 months, optionally at least about 5 months, optionally at least about 6 months. Structural integrity may be assessed by, for example, the bioabsorbable material retaining least 50% of its mass for the specified time, and/or retaining at least about 50% of its tensile strength for the specified time.

The material may be, but is not limited to, a bioabsorbable electrospun polymer or a matrix with one or more supramolecular compounds. The matrix may be comprised of a fibrous network and at least 90% porosity, or at least 80% porosity, or at least 70% porosity, or at least 60% porosity.

The chordae replacement may be made of various including but not limited to a thread, multiple interwoven threads, a woven textile, a ribbon, a helix, a coil, or a combination thereof.

Additional information regarding suitable bioabsorbable material suitable is already described in preceding embodiments, and reference is made to that description for further details.

Figure 16:
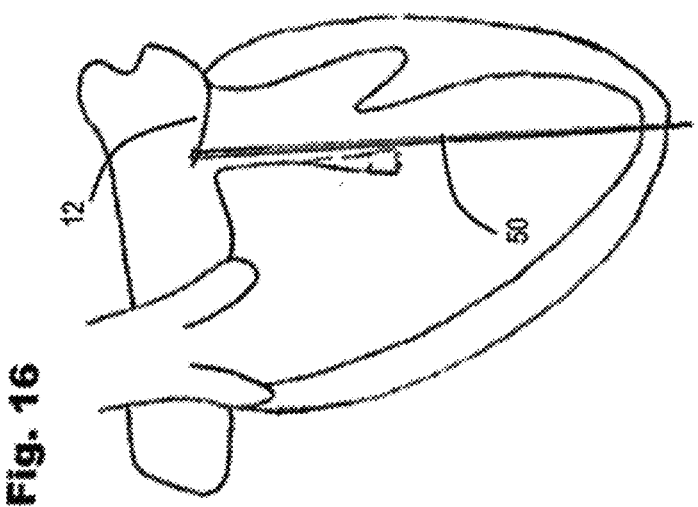

Referring to FIGS. 13 to 18, in some embodiments, an implantation technique may include, but is not limited to, inserting a delivery system 52 through the apex of the heart into the left ventricle 32 (FIGS. 13 and 14), grabbing the prolapsed mitral leaflet 12 (FIG. 14), piercing through the leaflet 12 and inserting the distal end of the chordae replacement 50 along with an anchor 22 or a pledget or other means (FIG. 15). The anchor 22 or the pledget located on the atrial side of the prolapsed leaflet may act as a stress distributor and therefore distributing the load over the surface of the anchor 22 or pledget. The delivery system is removed leaving the replacement chordae passing through the apex (FIG. 16). With the chordae replacement 50 secured onto the prolapsed leaflet 12, the chordae 50 is pulled in order to correct and therefore eliminate the prolapse (FIG. 17) and the chordae replacement 50 is then secured either onto the inner wall of the apex or outside the apex (FIG. 18) by various means such as, but not limited, to suturing or stapling.

The adjustment of the tension of the chordae replacement 50 may be done either geometrically by determining before hand the length of the chord needed for optimal leaflet coaptation or can be performed live using echo or fluoroscopy thereby ensuring no leakage and prolapse is taking place.

Instead of one chordae replacement, one may also use a similar implantation technique to place a loop, in other words two chordae, instead of just one. One may also us the same implantation technique and place multiple chords if need be at various location if a more optimal leaflet performance can be achieved.

The implantation may also be performed using a different access other than a transapical access if a different access site is preferred. Grabbing of the leaflet may be performed by various means including but not limited to deployment of two fingers to clamp onto the leaflet or bringing a suction device close to the leaflet to grab it.

Vascular Closure Device

Additionally or alternatively to any of the preceding embodiments, other embodiments of the disclosure may provide a VCD comprising bioabsorbable material.

Referring to FIGS. 1 to 12, the bioabsorbable material may provide structural integrity for the VCD 60. For example, the bioabsorbable material may provide a load-bearing structure of the VCD 60.

The bioabsorbable material may have a tensile strength at least about 0.1 MPa, optionally at least about 0.5 MPa, optionally at least about 1 MPa, optionally at least about 5 MPa, optionally at least about 10 MPa, optionally at least about 20 MPa, optionally at least about 50 MPa.

The bioabsorbable material may have a suture retention capability of at least about 0.5 Newton, optionally at least about 1 Newton, optionally at least about 2 Newton, optionally at least about 5 Newton, optionally at least about 10 Newton.

The bioabsorbable material may have a degradation rate after implantation in the body such that the bioabsorbable material retains its structural integrity for at least about 1 week, optionally at least about 2 weeks, optionally at least about 1 month, optionally least about 2 months. Structural integrity may be assessed by, for example, the bioabsorbable material retaining least 50% of its mass for the specified time, and/or retaining at least about 50% of its tensile strength for the specified time.

The VCD 60 may be made at least partly of the material, or at least a majority of the VCD 60 may be of the material, or substantially all of the VCD may be of the material.

The material may be, but is not limited to, a bioabsorbable electrospun polymer or a matrix with one or more supramolecular compounds. The matrix may be comprised of a fibrous network and at least 90% porosity, or at least 80% porosity, or at least 70% porosity, or at least 60% porosity.

Additional information regarding suitable bioabsorbable material suitable is already described in preceding embodiments, and reference is made to that description for further details.

The VCD 60, once deployed may optionally comprise a shape selected from, but not limited to, a dumbbell, a cork, a double parachute, an hourglass shape, or zig-zag shaped ribbon, or a plug, a rivet, or any combination of two or more of these shapes.

The VCD 60 may also be used in conjunction with sutures, which could in turn be biodegradable and or thin biodegradable rods, for added safety and enhanced control.

Figure 1:
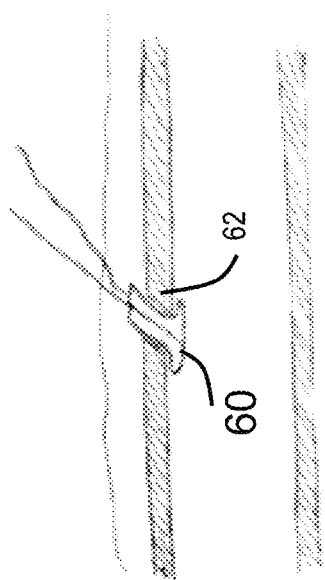
FIGS. 1 to 6 are schematic drawings illustrating deployment of an example VCD with a dedicated or a conventional sheath.
Figure 2:
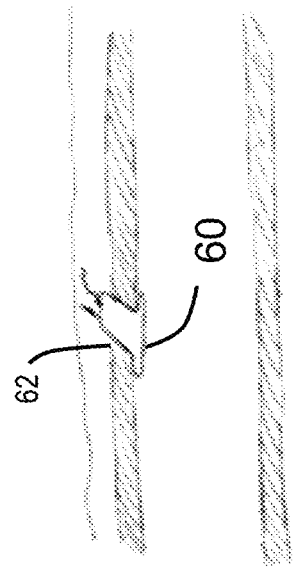
Figure 3:
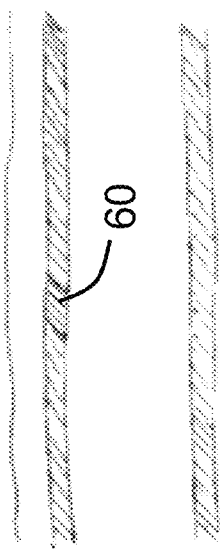
Figure 4:
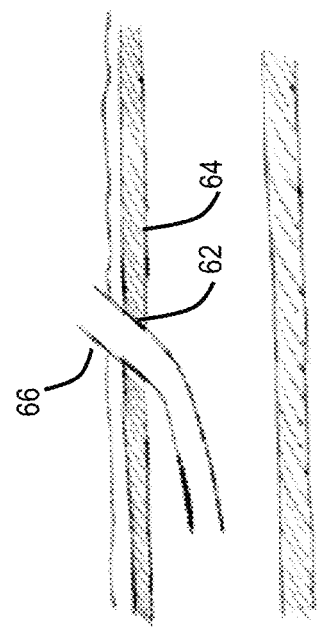
Figure 5:
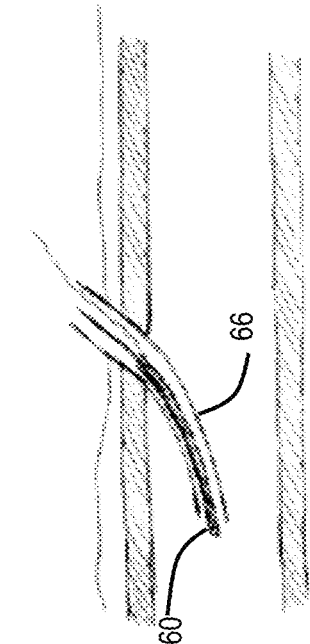
Figure 6:
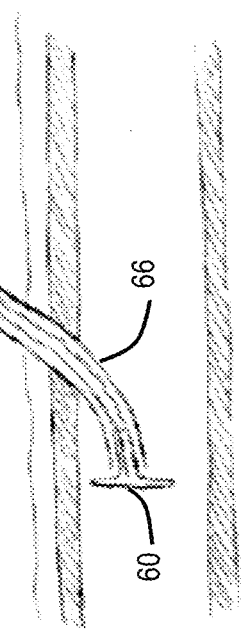
Figure 7:
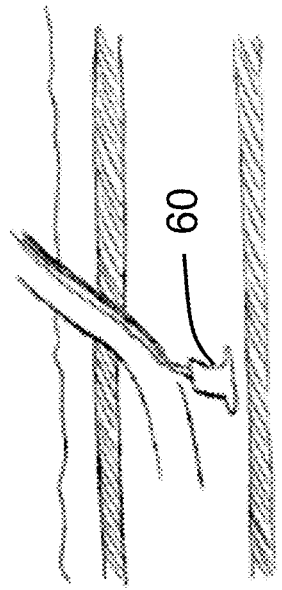
FIGS. 7 to 12 are schematic drawings similar to FIGS. 1 to 6, illustrating an example deployment of the VCD with a dedicated sheath with a side port for pre-placement of the closure device.
Figure 8:
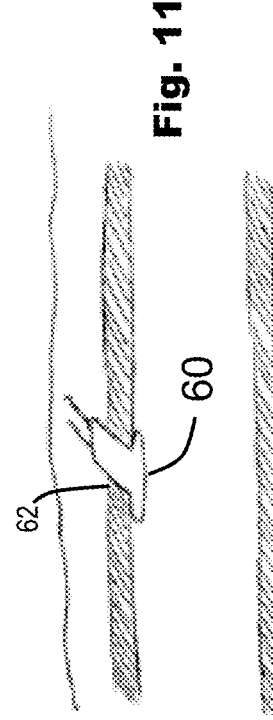
Figure 9:
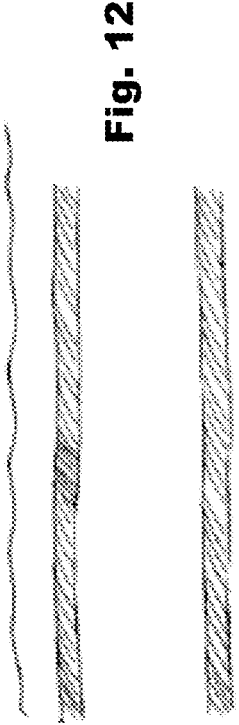
Figure 10:
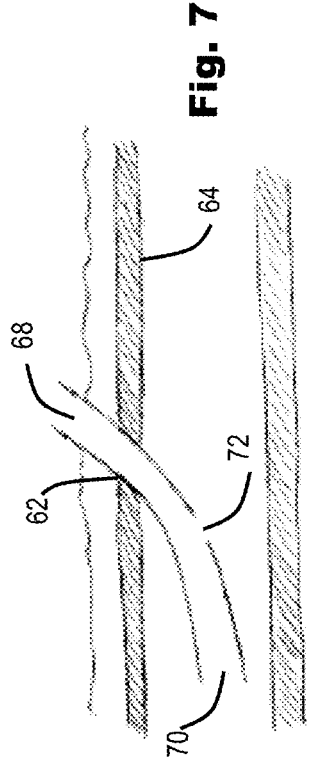

Referring to FIG. 1, In some embodiments, the VCD 60 may be used to seal an access hole 62 in an artery or vein 64 into which an access sheath 66 has been inserted. The implantation technique for placing the VCD may include, but is not limited to, inserting the distal end of the VCD 60 in a collapsed state into the artery or vein through the sheath 66 and/or access hole 62 (FIG. 2), releasing the distal end of the VCD 60 in the artery thereby either actively or passively deploying the distal end of the VCD 60 (FIG. 3), pulling on the VCD 60 with a means including but not limited to the use of a biodegradable suture or the catheter in order to ensure the deployed distal end of the VCD is firmly lodged in the artery and firmly pressed again the access hole 62 to ensure sealing (FIG. 4), further releasing the proximal end of the VCD to fully deploy it (FIG. 5), removing the control means which could be combined with cutting the biodegradable sutures if used under the skin, and finally closing the skin with conventional techniques (FIG. 6). With time, the VCD will be absorbed into the arterial wall tissue.

In terms of working sheath, the sheath 66 used to insert the VCD 60 could be a dedicated sheath inserted at the beginning of the intervention, which can be used for the diagnostic procedure or the intervention. The VCD 60 may also be provided as a stand-alone compatible with diagnostic and interventional sheath.

Figure 11:
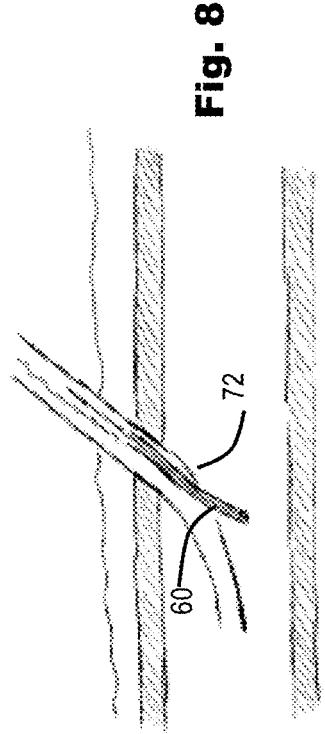
Figure 12:
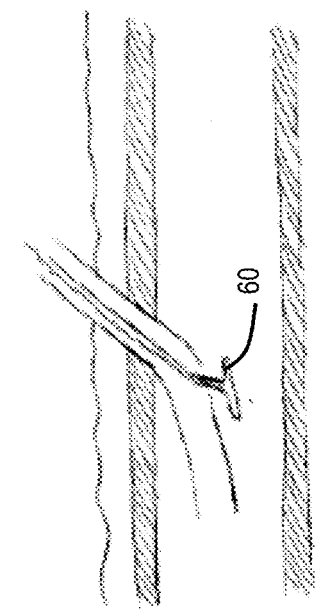
Figure 18:
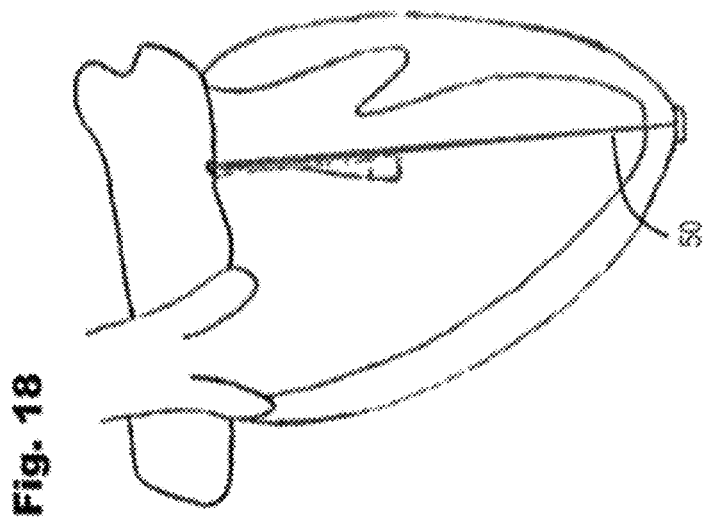
Figure 17:
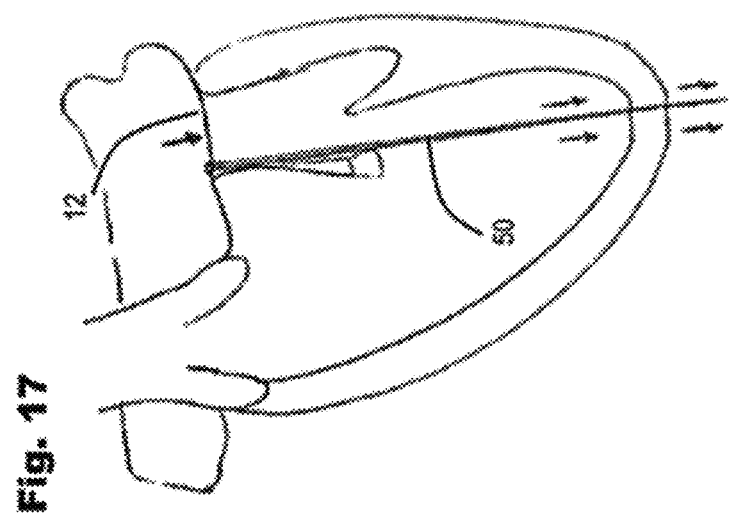

Referring to FIGS. 7 to 12, if speed from end of procedure to vascular closure is needed, a dedicated sheath 68 with a distal port 70 for the diagnostic and intervention and a second side port 72 may be provided to allow for the deployment of the VCD 60 even before the procedure is started (FIGS. 7 and 8) The VCD 60 may then be quickly deployed immediately after the diagnostic or intervention is performed. For example, the VCD may be deployed while outside the side port 72 (FIGS. 9 and 10), and then pulled back with the sheath 68 and left in place in the access hole 62 (FIGS. 11 and 12).

An advantage of such a VCD 60 described herein is that it can provide structural integrity for a time period while the vascular tissue is healing, to support the access site. Such structural integrity may, in some cases, permit certain access at the same site, or an adjacent site, for re-intervention, even before the vascular tissue has healed. Over time, the bioabsorbable material is resorbed by the body, such that there is no permanent obstruction left at the access site, thereby restoring the possibility of full access to the same site.

Although certain aspects, features, ideas, and advantages have been described above, these are merely for the purpose of illustrating the invention(s), and do not limit the scope of the present disclosure.

What is claimed is:

1. An electrospun vascular closure device comprising: a stand-alone bioabsorbable fibrous network, wherein the bioabsorbable fibrous network has a tensile strength of at least about 0.1 MPa, a suture retention of at least about 0.5 N, and pores with a pore size in between 1 to 300 micrometers allowing cell infiltration and cell ingrowth throughout the thickness of the bioabsorbable fibrous network, wherein the bioabsorbable fibrous network has electrospun polymers, or a matrix with one or more supramolecular compounds with a fiber diameter of 1 micrometer to 50 micrometer, wherein the bioabsorbable fibrous network is an electropun material having a gradient in properties of the electrospun material, and wherein upon implantation the bioabsorbable fibrous network is capable of progressively being absorbed by a body and replaced by new tissue growth to replace the bioabsorbable fibrous network.

2. The vascular closure device as set forth in claim 1, wherein the bioabsorbable fibrous network has a coefficient of friction below 0.8.

3. An electrospun vascular closure device consisting essentially of: a stand-alone bioabsorbable fibrous network, wherein the bioabsorbable fibrous network has a tensile strength of at least about 0.1 MPa, a suture retention of at least about 0.5 N, and pores with a pore size in between 1 to 300 micrometers allowing cell infiltration and cell ingrowth throughout the thickness of the bioabsorbable fibrous network, wherein the bioabsorbable fibrous network has electrospun polymers, or a matrix with one or more supramolecular compounds with a fiber diameter of 1 micrometer to 50 micrometer, wherein the bioabsorbable fibrous network is an electropun material having a gradient in properties of the electrospun material, and wherein upon implantation the bioabsorbable fibrous network is capable of progressively being absorbed by a body and replaced by new tissue growth to replace the bioabsorbable fibrous network.

4. The vascular closure device as set forth in claim 3, wherein the bioabsorbable fibrous network has a coefficient of friction below 0.8.

5. An electrospun vascular closure device comprising: a stand-alone bioabsorbable fibrous network, wherein the bioabsorbable fibrous network has a tensile strength of at least about 0.1 MPa, a suture retention of at least about 0.5 N, and pores with a pore size in between 1 to 300 micrometers allowing cell infiltration and cell ingrowth throughout the thickness of the bioabsorbable fibrous network, wherein the bioabsorbable fibrous network has electrospun polymers, or a matrix with one or more supramolecular compounds with a fiber diameter of 1 micrometer to 50 micrometer, wherein the bioabsorbable fibrous network has a coefficient of friction below 0.8, and wherein upon implantation the bioabsorbable fibrous network is capable of progressively being absorbed by a body and replaced by new tissue growth to replace the bioabsorbable fibrous network.

6. The vascular closure device as set forth in claim 5, wherein the bioabsorbable fibrous network is an electropun material having a gradient in properties of the electrospun material.

7. An electrospun vascular closure device consisting essentially of: a stand-alone bioabsorbable fibrous network, wherein the bioabsorbable fibrous network has a tensile strength of at least about 0.1 MPa, a suture retention of at least about 0.5 N, and pores with a pore size in between 1 to 300 micrometers allowing cell infiltration and cell ingrowth throughout the thickness of the bioabsorbable fibrous network, wherein the bioabsorbable fibrous network has electrospun polymers, or a matrix with one or more supramolecular compounds with a fiber diameter of 1 micrometer to 50 micrometer, wherein the bioabsorbable fibrous network has a coefficient of friction below 0.8, and wherein upon implantation the bioabsorbable fibrous network is capable of progressively being absorbed by a body and replaced by new tissue growth to replace the bioabsorbable fibrous network.

8. The vascular closure device as set forth in claim 7, wherein the bioabsorbable fibrous network is an electropun material having a gradient in properties of the electrospun material.

* * * * *